(12) United States Patent
Ueda et al.

(10) Patent No.: US 10,842,911 B2
(45) Date of Patent: Nov. 24, 2020

(54) ALLOY MEMBER USABLE IN ORGANISMS AND PRODUCTION METHOD THEREFOR

(71) Applicants: FUJI LIGHT METAL CO., LTD., Kumamoto (JP); NATIONAL INSTITUTE OF ADVANCED INDUSTRIAL SCIENCE AND TECHNOLOGY, Tokyo (JP); MEL-FRONTIER, LTD., Tokyo (JP)

(72) Inventors: Hironori Ueda, Kumamoto (JP); Masashi Inoue, Kumamoto (JP); Kotaro Hanada, Tsukuba (JP)

(73) Assignees: FUJI LIGHT METAL CO., LTD., Kumamoto (JP); NATIONAL INSTITUTE OF ADVANCED INDUSTRIAL SCIENCE AND TECHNOLOGY, Tokyo (JP); MEL-FRONTIER, LTD., Tokyo (JP)

( * ) Notice: Subject to any disclaimer, the term of this patent is extended or adjusted under 35 U.S.C. 154(b) by 102 days.

(21) Appl. No.: 15/753,756

(22) PCT Filed: Aug. 18, 2016

(86) PCT No.: PCT/JP2016/074147
§ 371 (c)(1),
(2) Date: Feb. 20, 2018

(87) PCT Pub. No.: WO2017/030173
PCT Pub. Date: Feb. 23, 2017

(65) Prior Publication Data
US 2018/0264166 A1    Sep. 20, 2018

(30) Foreign Application Priority Data

Aug. 20, 2015    (JP) .................... 2015-163230

(51) Int. Cl.
*A61L 27/04*    (2006.01)
*A61L 27/58*    (2006.01)
(Continued)

(52) U.S. Cl.
CPC .......... *A61L 27/047* (2013.01); *A61L 17/00* (2013.01); *A61L 17/06* (2013.01); *A61L 27/04* (2013.01);
(Continued)

(58) Field of Classification Search
CPC ........ A61L 17/06; A61L 27/04; A61L 27/047; A61L 31/022; C23C 22/57; C23C 4/11;
(Continued)

(56) References Cited

U.S. PATENT DOCUMENTS 1,795,473 A    3/1931    Burdick
2004/0098108 A1    5/2004    Harder et al.
(Continued)

FOREIGN PATENT DOCUMENTS

EP    1 842 507 A1    10/2007
EP    2 630 978 A2    8/2013
(Continued)

*Primary Examiner* — Dinah Baria
(74) *Attorney, Agent, or Firm* — Studebaker & Brackett PC (57) ABSTRACT

Provided are an alloy member which is usable in organisms, makes use of features of bio-affinity and biodegradability of magnesium, and is able to realize required duration of biodegradability, and a production method therefor. According to the present invention, the alloy member usable in organisms includes a base body that contains a magnesium alloy, a first protective layer that contains an oxide derived from a component of the base body or a complex of an oxide and a hydroxide derived from a component of the base body, and a second protective layer that contains a hydroxide derived from a component of the base body.

9 Claims, 6 Drawing Sheets

(51) Int. Cl.
| | |
|---|---|
| C23C 22/57 | (2006.01) |
| C22C 23/04 | (2006.01) |
| C22C 23/06 | (2006.01) |
| A61L 17/00 | (2006.01) |
| A61L 31/00 | (2006.01) |
| C22C 23/00 | (2006.01) |
| C23C 22/83 | (2006.01) |
| C23C 28/04 | (2006.01) |
| C23C 22/73 | (2006.01) |
| A61L 17/06 | (2006.01) |
| A61L 27/50 | (2006.01) |
| A61L 31/02 | (2006.01) |
| A61L 31/14 | (2006.01) |

(52) U.S. Cl.
CPC ............. *A61L 27/507* (2013.01); *A61L 27/58* (2013.01); *A61L 31/00* (2013.01); *A61L 31/022* (2013.01); *A61L 31/148* (2013.01); *C22C 23/00* (2013.01); *C22C 23/04* (2013.01); *C22C 23/06* (2013.01); *C23C 22/57* (2013.01); *C23C 22/73* (2013.01); *C23C 22/83* (2013.01); *C23C 28/04* (2013.01)

(58) Field of Classification Search
CPC ......... C23C 14/081; A61F 2310/00197; A61F 2310/00598
See application file for complete search history.

(56) References Cited

U.S. PATENT DOCUMENTS

| | | |
|---|---|---|
| 2004/0241036 A1* | 12/2004 | Meyer-Lindenberg ..................... A61L 27/047 420/405 |
| 2008/0262589 A1 | 10/2008 | Nagura |
| 2009/0081313 A1 | 3/2009 | Aghion et al. |
| 2013/0195714 A1 | 8/2013 | Lyon |
| 2013/0218292 A1 | 8/2013 | Bayer et al. |
| 2013/0261735 A1* | 10/2013 | Pacetti .................... A61F 2/915 623/1.36 |
| 2014/0222133 A1 | 8/2014 | Stekker et al. |
| 2014/0371059 A1 | 12/2014 | O'Keefe et al. |

FOREIGN PATENT DOCUMENTS

| | | |
|---|---|---|
| JP | 2004-160236 A | 6/2004 |
| JP | 2006-167078 A | 6/2006 |
| JP | 2008-125622 A | 6/2008 |
| JP | 2009-535504 A | 10/2009 |
| JP | 2013-524004 A | 6/2013 |
| WO | 2006/080381 A1 | 8/2006 |
| WO | 2011/117628 A1 | 9/2011 |
| WO | 2013/024124 A1 | 2/2013 |

* cited by examiner

| Mg-2Nd-1Y-0.5Mn-0.5Zn-0.4Zr | ELONGATION | UTS |
|---|---|---|
| | % | MPa |
| ROLLED MATERIAL A | 19 | 303 |
| ROLLED MATERIAL B (HEAT TREATMENT 350°C×30min) | 22 | 290 |
| EXTRUDED MATERIAL C | 35 | 210 |

FIG. 13

| Mg-2Nd-1Y-0.5Mn-0.5Zn-0.4Zr | WEIGHT REDUCTION PERCENTAGE | CORROSION RATE |
|---|---|---|
| | % | mm/y |
| UNTREATED | 2.39 | 2.95 |
| SURFACE-TREATED MATERIAL | 0.91 | 1.10 |

FIG. 14

COMPLEX OF HYDROXIDES OF Mg, Nd, AND Gd
COMPLEX OF OXIDES OF Mg, Nd, AND Gd
THICKNESS OF 200 nm
BASE BODY
EXAMPLE 2

FIG. 15

| Mg-2.5Nd-1Gd-0.4Zr | WEIGHT REDUCTION PERCENTAGE | CORROSION RATE |
|---|---|---|
| | % | mm/y |
| UNTREATED | 3.23 | 2.20 |
| SURFACE-TREATED MATERIAL | 2.64 | 1.68 |

FIG. 16

| PERIOD OF IMMERSION (WEEKS) | UNTREATED MATERIAL | | SURFACE-TREATED MATERIAL | |
|---|---|---|---|---|
| | WEIGHT REDUCTION PERCENTAGE (%) | CORROSION RATE (mm/y) | WEIGHT REDUCTION PERCENTAGE (%) | CORROSION RATE (mm/y) |
| 0 | — | — | — | — |
| 1 | 6.6 | 0.8 | 1.0 | 0.1 |
| 2 | 32.0 | 2.1 | 5.8 | 0.4 |
| 3 | 5.6 | 0.2 | 3.8 | 0.2 |
| 4 | 33.3 | 1.1 | 6.1 | 0.2 |
| 5 | 36.0 | 1.0 | 9.6 | 0.3 |
| 6 | 34.7 | 0.8 | 11.0 | 0.2 |
| 7 | 48.2 | 0.9 | 10.3 | 0.2 |
| 8 | 30.2 | 0.5 | 10.1 | 0.2 |
| 9 | 40.9 | 0.6 | 7.7 | 0.1 |

ALLOY MEMBER USABLE IN ORGANISMS AND PRODUCTION METHOD THEREFOR

TECHNICAL FIELD

The present invention relates to an alloy member usable in organisms such as humans and animals, and a production method therefor.

BACKGROUND ART

In humans, animals, and the like, various members are used in an organism for therapy for disease or injuries, prevention of disease or injuries, and the like. For example, members coping with suturing a cut portion, binding a bone-fracture portion, an artificial blood vessel, a vascular stent, and a part of an artificial joint are used. In other words, these members are biocompatible implants (biocompatible implants for therapy, prevention, or the like).

Some of the members are formed of raw materials derived from an organism, and some thereof are formed of raw materials not derived from an organism. This is because there are many difficulties in forming the members with raw materials derived from an organism in regard to supply of raw materials, production costs, and the like. In order to cope with such difficulties, the members have begun to be formed with raw materials other than those derived from an organism.

For example, vascular stents, which are produced with a metal having an easy production step, having high production precision and production quality, and being able to be suppressed in production costs as a raw material, have begun to be proposed.

For example, a vascular stent is inserted into a blood vessel of an organism having a symptom such as cardiac infarction or brain infarction. The vascular stent has a predetermined inner diameter and is able to mitigate a symptom such as cardiac infarction or brain infarction by dilating the contracted blood vessel.

On the other hand, in a case where skin or body tissue is cut due to an injury or a surgical operation, a suturing member suturing the cut portion is used. Recently, in addition to so-called sutures, a member such as a stapler is sometimes used for suturing. Naturally, sutures are sometimes used as well.

Meanwhile, for therapy for bone fracture or the like, a binding member (a fixing bolt or the like) binding fractured bones together is sometimes used in organisms as well.

Many of biocompatible members preferably dissipate with time. This is because a vascular stent, a suturing member, a binding member, or the like is no longer necessary for an organism, since biological tissue recuperates biologically. Therefore, it is preferable that the biocompatible members dissipate after a period of time during which an organism recuperates biologically.

On the other hand, some artificial blood vessels need only be used for a temporary period of time until a blood vessel derived from an organism takes the place thereof. In such a case as well, there are cases where service durability is required during the temporary period of time and the artificial blood vessel may dissipate or the like thereafter.

In this way, for therapy or prevention for organisms, there is an increasing demand for members which have service durability during a certain period of time required for therapy or prevention and dissipate or are degraded after the certain period of time elapses.

As a method of forming such a member usable in organisms (a member used in therapy or prevention), technologies of using a metal as a raw material thereof have been proposed (for example, refer to Patent Document 1, Patent Document 2, and Patent Document 3).

CITATION LIST

Patent Document

Patent Document 1: Japanese Patent Application Laid-Open No. 2004-160236
Patent Document 2: PCT Japanese Translation Patent Publication No. 2009-535504
Patent Document 3: Japanese Patent Application Laid-Open No. 2006-167078

SUMMARY

Technical Problem

Patent Documents 1, 2, and 3 each have proposed a technology of forming endoprostheses and medical implants having magnesium as one of their raw materials. Patent Documents 1 to 3 each have proposed to form a biocompatible member having magnesium as one of raw materials thereof, because magnesium is one of the components contained in organisms and has favorable affinity with organisms. Therefore, Patent Documents 1 to 3 each have proposed to form a biocompatible member such as an endoprosthesis and a medical implant having magnesium as one of raw materials thereof.

Patent Document 1 discloses an endoprosthesis having a support structure which contains a metal material including a magnesium alloy as follows.
Magnesium: more than 90%
Yttrium: 3.7% to 5.5%
Rare earths: 1.5% to 4.4%
Remainder: less than 1%

An object of Patent Document 1 is to provide an endoprosthesis which has high bio-affinity by having magnesium as a main component. Moreover, another object thereof is to provide an endoprosthesis which is degraded and dissipates after attachment by having magnesium characterized by high degradability as a main component.

However, an endoprosthesis having magnesium as a main component (magnesium alloy) reacts to water inside biological tissue, and is degraded while generating a magnesium hydroxide and hydrogen. In the endoprosthesis disclosed in Patent Document 1, a magnesium alloy is exposed on a surface thereof, and the degradation while generating a magnesium hydroxide and hydrogen proceeds quickly. Therefore, the endoprosthesis disclosed in Patent Document 1 has a problem that it is not possible for the endoprosthesis to sustain an endurance period which is desired to be sustained.

For example, if the endoprosthesis is a vascular stent, an endurance period of approximately half a year is required. However, the endoprosthesis disclosed in Patent Document 1 is unlikely to endure this endurance period. This is because duration of biodegradability is short.

In addition, an endoprosthesis used in organisms is required to have sufficient mechanical strength and processability in accordance with a usage object thereof. However, since the endoprosthesis disclosed in Patent Document 1 is formed of only an alloy having magnesium as a main component, there is a limit to the mechanical strength. If the limit is intended to be improved, there is also occurrence of a problem that the endurance period is not able to be sufficiently lengthened.

Insufficient duration of biodegradability also leads to strength deficiency of a biocompatible member. Insufficient duration of biodegradability results in a problem that strength required in a location where a biocompatible member is to be used is not able to be retained for a required period of time in a case where the biocompatible member is used by being embedded in a human body or an animal. For example, in a case where a biocompatible member formed of magnesium is used in a vascular stent, sometimes the biocompatible member is no longer able to endure a contract symptom of a blood vessel and is squashed before therapy is completed. In other application cases as well, insufficient duration of biodegradability may cause a problem that a biocompatible member is squashed, damaged, and broken without fulfilling a required therapeutic period. In other words, Patent Document 1 does not have sufficient strength with respect to application locations or purposes.

Meanwhile, if the thickness of a biocompatible member applied as a vascular stent or the like is increased in order to cope with this strength deficiency, the biocompatible member is unlikely to be installed in an application location. For example, in a case of a vascular stent, the vascular stent is delivered to an artery or the like through a catheter. However, in a case where the thickness thereof is increased, it may be difficult to perform the operation. Otherwise, the inner diameter thereof sometimes becomes excessively small inside a blood vessel after installation so that a blood flow is hindered.

Therefore, deficient strength is not adequate for the biocompatible member.

Moreover, as described above, if an endoprosthesis is degraded while generating a magnesium hydroxide and hydrogen, there is a problem that the pH value inside an organism increases so that the organism is in an alkaline environment. On the other hand, derived hydrogen may cause a problem such as generating air bubbles inside a biological tissue.

Patent Document 2 discloses a biodegradable magnesium alloy which contains magnesium of at least 90 percent by weight, neodymium ranging from 1.5 percent by weight to 5 percent by weight, yttrium ranging from 0.1 percent by weight to 4 percent by weight, zirconium ranging from 0.1 percent by weight to 1 percent by weight, and calcium ranging from 0.1 percent by weight to 2 percent by weight, and contains no zinc.

Similar to Patent Document 1, Patent Document 2 also discloses a magnesium alloy having magnesium as a main component, that is, a biodegradable magnesium alloy which, in a case of being used in an organism, is degraded inside the organism.

In Patent Document 2 as well, similar to Patent Document 1, a biocompatible member is formed of only a magnesium alloy having magnesium as a main component. Therefore, if the biocompatible member is used in an organism, there is a problem that reaction to water inside the organism proceeds in a short period of time so that the biocompatible member is degraded and dissipates very quickly. In addition to this problem, there is another problem of deficient mechanical strength.

Therefore, Patent Document 2 has problems similar to those of Patent Document 1.

Patent Document 3 discloses a medical implant having an implant body formed of a magnesium metal material containing lithium ranging from 5.7% to 22.2% by mass and zirconium of 1% or less by mass.

An object of Patent Document 3 is also to provide a medical implant (biocompatible member) in which magnesium alloy having magnesium as a main component is used. Here, high bio-affinity and biodegradability of magnesium are utilized. In this regard, the technology of Patent Document 3 is similar to those of Patent Documents 1 and 2.

The medical implant of Patent Document 3 is also formed of only a magnesium alloy. Therefore, biodegradability is prioritized, and there is a problem that reaction to water inside an organism proceeds in a short period of time so that the medical implant is degraded and dissipates very quickly. In addition to this problem, there is another problem of deficient mechanical strength.

Therefore, Patent Document 3 has a problem similar to that of Patent Document 1.

As above, the technologies in the related art disclosed in Patent Documents 1 to 3 disclose biocompatible members targeting biodegradability and bio-affinity of magnesium. However, as a result of the structures in which only the biodegradability and bio-affinity are prioritized, there is a problem that duration of biodegradability (endurance period) is insufficiently ensured.

The insufficient duration of biodegradability leads to a problem that it is not possible to sufficiently realize the purpose as a biocompatible member, and durability or strength required in an application location.

Moreover, biodegradation, which proceeds in a short period of time, causes other problems such as a change in an alkaline environment of an organism or air bubbles generated inside an organism, so that it is difficult for the members to be used as biocompatible members.

As a result of those described above, the biocompatible members using magnesium or a magnesium alloy according to the technologies in the related art disclosed in Patent Documents 1 to 3 have a problem of difficulties in being used for required purposes or application locations.

In consideration of the foregoing tasks, an object of the present invention is to provide an alloy member which is usable in organisms, makes use of features of bio-affinity and biodegradability of magnesium, and is able to realize required duration of biodegradability, and a production method therefor.

Solution to Problem

In consideration of the foregoing tasks, according to the present invention, there is provided an alloy member usable in organisms including a base body that contains a magnesium alloy, a first protective layer that contains an oxide derived from a component of the base body or a complex of an oxide and a hydroxide derived from a component of the base body, and a second protective layer that contains a hydroxide derived from a component of the base body.

Advantageous Effects of Invention

The alloy member usable in organisms according to the present invention is an alloy member which has high affinity or adaptability with respect to organisms (including biological tissue and biological cells) and is usable for various purposes, for example, artificial blood vessels, vascular stents, suturing members, and binding members.

In addition, the alloy member of the present invention is biodegradable. On the other hand, the protective layers are formed on the surface of the base body having magnesium as a main component, so that it is possible to lengthen the duration of biodegradability. Particularly, it is possible to cause reaction of the alloy member to biological tissue water inside an organism to proceed slowly. Accordingly, dissimilar to the technologies in the related art, it is possible to cause biodegradation to proceed slowly. Consequently, it is possible to realize duration of biodegradability that covers a required period of time to be used for various purposes.

In addition, due to components of the protective layers, the base body having magnesium as a main component generates an oxide or a hydroxide during a process in which the protective layers are removed. As a result thereof, although the protective layers are removed, biodegradation of the alloy member proceeds slowly. Consequently, it is possible to lengthen the duration of biodegradability.

In addition, due to protection by the protective layers, it is possible to perform design and processing such that the base body having magnesium as a main component sufficiently realizes mechanical strength required when being used in organisms. Consequently, it is possible to use the alloy member for various purposes and in various application locations in therapy or prevention for organisms.

DESCRIPTION OF EMBODIMENTS

According to a first aspect of the present invention, there is provided an alloy member usable in organisms including a base body that contains a magnesium alloy, a first protective layer that contains an oxide derived from a component of the base body or a complex of an oxide and a hydroxide derived from a component of the base body, and a second protective layer that contains a hydroxide derived from a component of the base body.

According to the configuration, the alloy member usable in organisms is able to achieve both high affinity of the magnesium alloy with respect to organisms, and duration of biodegradability lengthened due to the first protective layer and the second protective layer. As a result of those described above, when the alloy member is used in organisms, it is possible to realize service durability coping with a required therapeutic period.

According to the configuration, the alloy member usable in organisms is able to be applied to various purposes necessary for therapy for organisms and prevention of disease. Particularly, it is possible to optimally use the alloy member even in a case of being internally applied to organisms.

In the alloy member usable in organisms according to a second aspect of the present invention, in addition to the first aspect, the base body contains a magnesium alloy realized by adding a mixture to magnesium.

According to the configuration, the base body is able to highly achieve both bio-affinity of magnesium and binding properties with respect to the protective layers. Moreover, in the base body, even after the first protective layer and the second protective layer are exfoliated, it is possible to form a protective layer by efficiently causing reaction to water.

In the alloy member usable in organisms according to a third aspect of the present invention, in addition to the second aspect, the mixture contains at least one of predetermined rare earth elements and at least one of predetermined non-rare earth elements.

According to the configuration, in the base body, it is possible to increase binding force with respect to the first protective layer and the like by generating an intermetallic compound. Furthermore, even after the first protective layer and the like are exfoliated, it is possible to delay corrosion by forming a layer of an oxide or a hydroxide due to reaction to water of an organism.

In the alloy member usable in organisms according to a fourth aspect of the present invention, in addition to the third aspect, the predetermined rare earth elements each have activation energy of 1,000 kJ/mol or greater in a case of being oxidized to become an oxide.

In the alloy member usable in organisms according to a fifth aspect of the present invention, in addition to the third or fourth aspect, the predetermined non-rare earth elements each have activation energy of 1,000 kJ/mol or greater in a case of being oxidized to become an oxide.

According to the configurations, the base body is able to efficiently generate an oxide or a hydroxide due to reaction to water of an organism. An oxide or a hydroxide thereof serves as a protective layer of the base body so that it is possible to delay corrosion of the base body.

In the alloy member usable in organisms according to a sixth aspect of the present invention, in addition to any one of the third to fifth aspects, the predetermined rare earth elements contain any one of Sc, Y, Dy, Sm, Ce, Gd, and La.

According to the configuration, rare earth elements contained in the base body are able to generate a layer of an oxide or a hydroxide due to reaction to water of an organism. The efficiency in generation is also favorable.

In the alloy member usable in organisms according to a seventh aspect of the present invention, in addition to any one of the third to sixth aspects, the predetermined non-rare earth elements contain any one of Ti, Ta, Nb, Al, Mn, Fe, Cr, B, P, V, and Zr.

According to the configuration, non-rare earth elements contained in the base body are able to generate a layer of an oxide or a hydroxide due to reaction to water of an organism. The efficiency in generation is also favorable.

In the alloy member usable in organisms according to an eighth aspect of the present invention, in addition to any one of the first to seventh aspects, the first protective layer is formed on a surface of the base body, and the second protective layer is formed on a surface of the first protective layer.

According to the configuration, the first protective layer and the second protective layer are able to cooperatively reduce water reaching the base body.

In the alloy member usable in organisms according to a ninth aspect of the present invention, in addition to any one of the first to eighth aspects, the oxide of the first protective layer includes at least any of an oxide of magnesium, an oxide of rare earths, and an oxide of non-rare earths.

According to the configuration, the first protective layer is able to enhance binding force with respect to the base body. The first protective layer becomes a stabler layer and is able to reduce water reaching the base body.

In the alloy member usable in organisms according to a tenth aspect of the present invention, in addition to any one of the first to ninth aspects, the complex of an oxide and a hydroxide of the first protective layer includes an oxide of magnesium and a hydroxide of magnesium.

According to the configuration, the first protective layer enhances the binding degree with respect to the base body and becomes a stable layer.

In the alloy member usable in organisms according to an eleventh aspect of the present invention, in addition to any one of the first to tenth aspects, the hydroxide of the second protective layer includes a hydroxide of at least any of magnesium, rare earths, and non-rare earths.

According to the configuration, the second protective layer becomes a very elaborate and stable layer. As a result thereof, the second protective layer is able to reduce water reaching the base body.

In the alloy member usable in organisms according to a twelfth aspect of the present invention, in addition to any one of the first to eleventh aspects, the base body is able to form at least one of a hydroxide and an oxide due to water inside biological tissue.

According to the configuration, even after the first protective layer or the second protective layer is exfoliated, the base body forms a layer of an oxide or a hydroxide, so that it is possible to lengthen the duration of biodegradability.

In the alloy member usable in organisms according to a thirteenth aspect of the present invention, in addition to any one of the first to twelfth aspects, the base body contains Nd ranging from 0.5 to 5.0 percent by weight, Y ranging from 0.1 to 5.0 percent by weight, Mn ranging from 0.1% to 1.0%, Zn ranging from 0.1 to 4.0 percent by weight, and Zr ranging from 0.1 to 1.0 percent by weight.

In the alloy member usable in organisms according to a fourteenth aspect of the present invention, in addition to any one of the first to thirteenth aspects, the base body contains Nd ranging from 0.5 to 5.0 percent by weight, Gd ranging from 0.1 to 5.0 percent by weight, and Zr ranging from 0.1 to 1.0 percent by weight.

According to the configurations, the base body is able to optimally exhibit functions thereof.

In the alloy member usable in organisms according to a fifteenth aspect of the present invention, in addition to the first to fourteenth aspects, the alloy member is used in a bio-implantation device or the like which requires biodegradability.

In the alloy member usable in organisms according to a sixteenth aspect of the present invention, in addition to the first to fifteenth aspects, the alloy member is used in at least one of an artificial blood vessel, a stent, a suturing material for organisms, a vascular embolic coil, a clip, an encapsulant, a binding material for organisms, a binding material for bones, a mesh sheet, a correction material for bones, a solid or porous support material for bones, and a scaffold in which cells are retained and proliferate inside an organism.

In the alloy member usable in organisms according to a seventeenth aspect of the present invention, in addition to the first to sixteenth aspects, the alloy member is used for regenerative medicine.

According to the configurations, the alloy member usable in organisms is able to be applied to various purposes necessary for therapy for organisms and prevention of disease. Particularly, it is possible to optimally use the alloy member even in a case of being internally applied to organisms.

Hereinafter, with reference to the drawings, embodiments of the present invention will be described.

Embodiment 1

(Overview)

Figure 1:
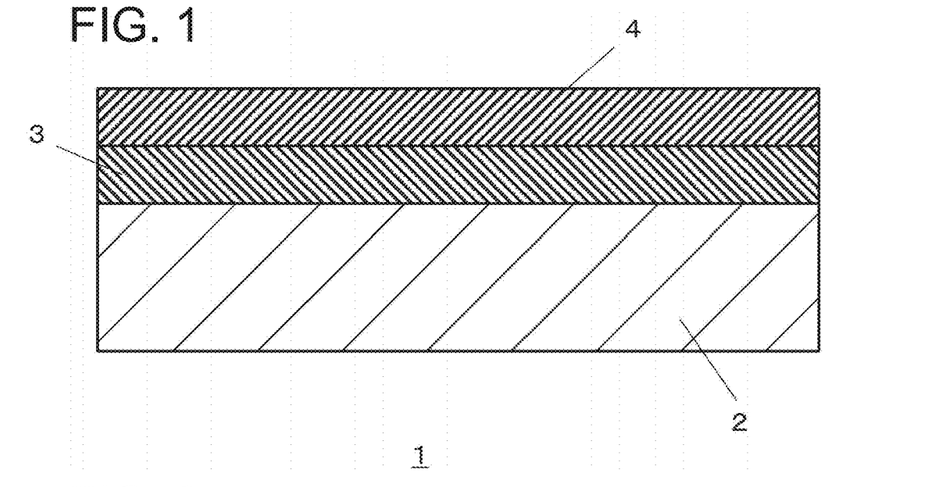
FIG. 1 is a schematic view of a biocompatible alloy member in Embodiment 1 of the present invention.

First, an overview of an alloy member usable in organisms in Embodiment 1 (which will hereinafter be referred to as a "biocompatible alloy member") will be described. FIG. 1 is a schematic view of a biocompatible alloy member in Embodiment 1 of the present invention. FIG. 1 schematically illustrates a cross section of a biocompatible alloy member 1.

As described below, it is possible to use the biocompatible alloy member 1 for various purposes inside the body or on a surface of the body of humans and animals (living things). In this case, the biocompatible alloy member 1 has a shape corresponding to the purpose thereof. Here, while corresponding to the shape and the purpose, the biocompatible alloy member 1 has a cross section as illustrated in FIG. 1. The biocompatible alloy member 1 with such a cross section has a shape corresponding to the purpose and the application location.

In the present invention, the biocompatible alloy member 1 includes a case of being a member which is processed into a state where the member is used for various purposes in various locations of an organism and a case of being a member before being processed into a state where the member is used in an organism. For example, in a case where the biocompatible alloy member 1 is a vascular stent, the biocompatible alloy member 1 is in a state of being processed to have a shape and a size as the vascular stent. On the other hand, in a case where the biocompatible alloy member 1 is used in a vascular stent or the like after being processed, the biocompatible alloy member 1 is in a state before being processed.

In this way, the biocompatible alloy member 1 of the present invention need only be in a state of having the cross-sectional characteristics in FIG. 1, and includes a state before being processed for the purpose of use in organisms and a state after being processed.

In addition, the alloy member 1 is used in a bio-implantation device which requires biodegradability. For example, the alloy member 1 is used in an artificial blood vessel, a stent, a suturing material for organisms, a vascular embolic coil, a clip, an encapsulant, a binding material for organisms, a binding material for bones, a mesh sheet, a correction material for bones, a solid or porous support material for bones, and a scaffold in which cells are retained and proliferate inside an organism. Furthermore, for example, these are utilized in regenerative medicine and the like.

The biocompatible alloy member 1 includes a base body 2 in which a magnesium alloy is used, a first protective layer 3, and a second protective layer 4. The first protective layer 3 is a top layer of the base body 2. The second protective layer 4 is a top layer of the first protective layer 3.

The first protective layer 3 is an oxide derived from a component of the base body 2 or a complex of an oxide and a hydroxide. Since a magnesium alloy is used in the base body 2, the first protective layer 3 is formed of an oxide derived from a component forming magnesium or a magnesium alloy. Alternatively, the first protective layer 3 is formed of a complex of an oxide and a hydroxide derived from a component forming magnesium or a magnesium alloy. For example, the first protective layer 3 is formed of oxidized magnesium. Alternatively, the first protective layer 3 is formed of a complex of oxidized magnesium and a magnesium hydroxide. In addition, the first protective layer 3 is formed of manganese hydroxide or the like derived from a component forming a magnesium alloy of the base body 2.

The second protective layer 4 is formed of a hydroxide derived from a component of the base body 2. Since a magnesium alloy is used in the base body 2, the second protective layer 4 is formed of a hydroxide derived from a component forming magnesium or a magnesium alloy. For example, the second protective layer 4 is formed of a magnesium hydroxide, a zinc hydroxide, or the like.

As illustrated in FIG. 1, the biocompatible alloy member 1 is formed in the order of the base body 2, the first protective layer 3, and the second protective layer 4. In other words, in the biocompatible alloy member 1, as a state of being exposed to the outside, the second protective layer 4 is exposed on the outermost circumference. The biocompatible alloy member 1 has a structure in which the base body 2 is in a state of not being exposed to the outside and the base body 2 is protected by the second protective layer 4 and the first protective layer 3.

If the biocompatible alloy member 1 is used in an organism, the outer circumference thereof is protected by the first protective layer 3 and the second protective layer 4 while having the base body 2 as a base portion. The second protective layer 4 is positioned on the outermost circumference and copes with an external influence first. The first protective layer 3 is provided between the second protective layer 4 and the base body 2 and protects the base body 2 following the second protective layer 4.

In this way, in the biocompatible alloy member 1 according to Embodiment 1, the first protective layer 3 and the second protective layer 4 are provided in the base body 2. As a result thereof, it is possible to ensure required duration of biodegradability. In other words, even in a case of being used for various locations and purposes in organisms, the biocompatible alloy member 1 has sufficient durability.

For example, the biocompatible alloy member 1 is used in at least one of an artificial blood vessel, a stent, a suturing member for organisms, a vascular embolic coil, a binding member for organisms, and a binding member for bones. Naturally, the biocompatible alloy member 1 may be used for purposes other than those enumerated herein.

Figure 2:
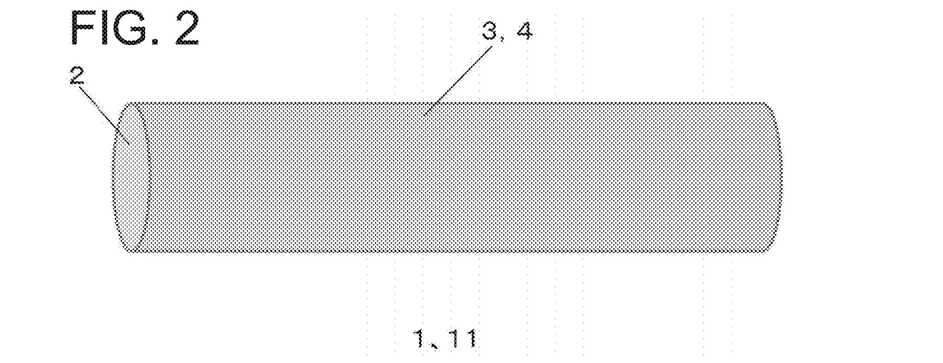
FIG. 2 is a perspective view of a case where a biocompatible alloy member is used in a vascular stent.

FIG. 2 is a perspective view of a case where a biocompatible alloy member is used in a vascular stent. The biocompatible alloy member 1 is processed to have a shape and a size required for a vascular stent 11. The vascular stent 11 has a columnar shape of which an internal space is penetrated. For example, due to the shape, the vascular stent 11 is inserted into an artery in which stenotic arteriosclerosis is caused. After being inserted thereinto, the vascular stent 11 widens the artery of a portion which is in a stenosed state, so that blood flows smoothly.

The biocompatible alloy member 1 used as the vascular stent 11 is used by being inserted into an artery. In the artery, the biocompatible alloy member 1 comes into contact with body fluid including blood of an organism. In other words, the biocompatible alloy member 1 comes into contact with water of an organism. The second protective layer 4 is a hydroxide derived from the base body 2 on the outermost circumference. The second protective layer 4 formed of a hydroxide has a very elaborate and stable structure.

Therefore, even in a case of being used as the vascular stent 11, in regard to contact with water in a blood vessel, the second protective layer 4 is able to restrain water from reaching the base body 2 as much as possible.

Furthermore, the first protective layer 3 is provided on the inner side of the second protective layer 4. The first protective layer 3 is an oxide derived from the base body 2 or a complex of an oxide and a hydroxide. The first protective layer 3 is a stable layer. Therefore, the first protective layer 3 is unlikely to allow water to reach the base body 2.

Figure 3:
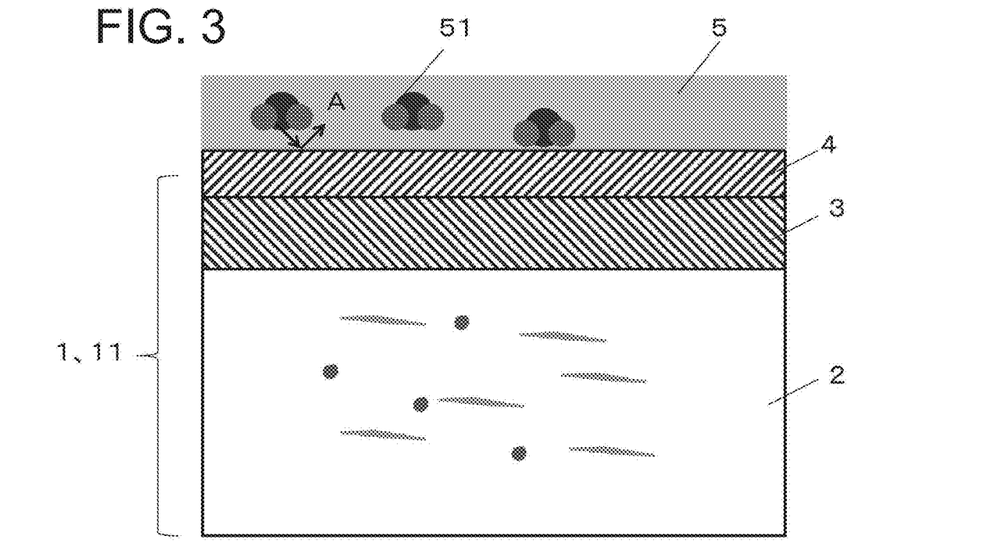
FIG. 3 is a schematic view of a vascular stent inserted into a blood vessel in Embodiment 1 of the present invention.

FIG. 3 is a schematic view of a vascular stent inserted into a blood vessel in Embodiment 1 of the present invention. The vascular stent 11 is inserted into a blood vessel and thereby comes into contact with blood 5. In addition, the vascular stent 11, which is a form of the above-described biocompatible alloy member 1, includes the base body 2, the first protective layer 3, and the second protective layer 4.

Here, the second protective layer 4 (outermost circumference) comes into contact with the blood 5. As described above, the second protective layer 4 is a very elaborate and stable layer. This is because the second protective layer 4 is formed of a hydroxide derived from the base body 2. For being a very elaborate and stable layer, the second protective layer 4 is able to prevent water 51 in the blood 5 from reaching the base body 2 as much as possible.

In addition, the first protective layer 3 on the inner side of the second protective layer 4 is a stable layer as well. The first protective layer 3 is also able to prevent the water 51 from reaching the base body 2 as much as possible. A dual structure of the first protective layer 3 and the second protective layer 4 cooperatively prevents the water 51 from reaching the base body 2 as much as possible.

The arrow A in FIG. 3 indicates a state where the water 51 is prevented from reaching the base body 2.

In this way, even in a case of being used as the vascular stent 11, in regard to contact with the blood 5, the biocompatible alloy member 1 according to Embodiment 1 is able to prevent the water 51 from reaching the base body 2 as much as possible. As a result thereof, it is possible to prolong deterioration caused due to reaction of the base body 2 formed of a magnesium alloy to water, as much as possible.

Figure 4:
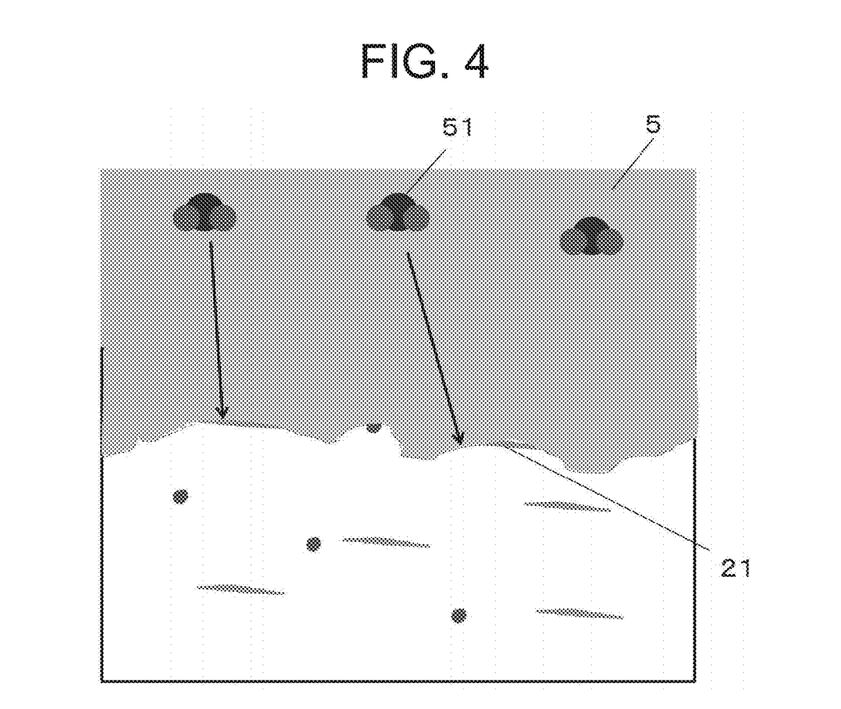
FIG. 4 is a schematic view of a vascular stent after a protective layer has been exfoliated in Embodiment 1 of the present invention.

Meanwhile, when a certain time elapses, the second protective layer 4 and the first protective layer 3 are each exfoliated due to reaction to the water 51. As a result of the exfoliation, the base body 2 is exposed, so that the base body 2 comes into direct contact with the blood 5. FIG. 4 is a schematic view of a vascular stent after a protective layer has been exfoliated in Embodiment 1 of the present invention. FIG. 4 illustrates a state where the first protective layer 3 and the second protective layer 4 are exfoliated due to reaction to the water 51.

In the vascular stent 11 (one of usage forms of the biocompatible alloy member 1) in a state of FIG. 4, the first protective layer 3 and the second protective layer 4 as distinct layers are exfoliated.

In a case where the base body 2 has come into contact with the water 51, the base body 2 begins to corrode due to reaction to the water 51. However, in the base body 2 during the process of corrosion, an intermetallic compound 21 which has been precipitated inside the alloy appears on a surface. Furthermore, an additive element included in the base body 2 reacts to water so that an oxide or a hydroxide is generated. These form an oxide layer, a hydroxide layer, or a protective layer thereof on a surface of the base body 2. The protective layer is an elaborate layer and is able to delay corrosion of the base body 2 caused due to the water 51.

In this way, even in a case where the first protective layer 3 and the second protective layer 4 are exfoliated due to reaction to the water 51, the base body 2 forms a hydroxide layer or the like and is able to delay corrosion caused due to reaction to the water 51. The protective layer described herein is generated if the base body 2 reacts to the water 51. Here, the base body 2 contains magnesium generating a magnesium alloy, or a component other than magnesium. Therefore, the protective layer generated due to reaction to water may be an oxide or a hydroxide derived from magnesium or an oxide or a hydroxide derived from a component other than magnesium contained in the magnesium alloy.

The protective layer is generated by a mixture of an oxide or a hydroxide.

Particularly, in the technologies in the related art, a protective layer derived from magnesium has been formed only, and a protective layer derived from various components has not been formed. Therefore, there has been a problem of insufficient durability. However, in the biocompatible alloy member 1 according to Embodiment 1, various components forming the base body react to water and are able to form a protective layer. Cooperatively with the first protective layer 3 and the second protective layer 4, it is possible to realize high service durability.

As above, even in a case where the biocompatible alloy member 1 is used in the vascular stent 11 and comes into contact with the blood 5, it is possible to delay corrosion as much as possible. In other words, it is possible to lengthen the duration of biodegradability and to improve the durability during the period of service. In a case where the biocompatible alloy member 1 is used in the vascular stent 11, the vascular stent 11 requires durability for a period of time during which therapy for arteriosclerosis is able to be performed. The biocompatible alloy member 1 of Embodiment 1 is able to realize service durability for the required period of time.

In this case, in the biocompatible alloy member 1, the second protective layer 4 which is a hydroxide derived from the base body 2 is able to prevent the water 51 from invading the base body 2. The second protective layer 4 is a very stable and elaborate layer. Due to the features, it is possible to prevent the water 51 from infiltrating into the base body 2. Moreover, for being a hydroxide, it is also possible to delay corrosion caused due to reaction to the water 51. Cooperatively with those described above, the second protective layer 4 is able to exhibit durability with respect to biodegradability and to delay exfoliation caused due to corrosion.

In addition, the first protective layer 3 is an oxide derived from the base body 2 or a complex of an oxide and a hydroxide derived from the base body 2. Since the first protective layer 3 is formed of a composition different from that of the second protective layer 4, the first protective layer 3 causes reaction to the water 51 different from that of the second protective layer 4. In other words, the first protective layer 3 reacts to the water 51 with a mechanism different from that of the second protective layer 4, so that it is possible to delay exfoliation caused due to corrosion. In addition, the first protective layer 3 is a stable layer and is able to prevent the water 51 from reaching the base body 2 as much as possible.

In this way, due to protection operated by a combination of the first protective layer 3 and the second protective layer 4 having characteristics different from each other, it is possible to prevent and reduce the water 51 reaching the base body 2. Since the water 51 is prevented from reaching the base body 2, it is possible to delay corrosion and degradation of the base body 2.

Subsequently, even in a case where the first protective layer 3 and the second protective layer 4 are exfoliated due to corrosion, a component contained in the base body 2 reacts to the water 51 and forms an elaborate oxide layer. The elaborate oxide layer is able to exhibit a function similar to that of the first protective layer 3. That is, it is possible to reduce infiltration of the water 51 into the base body 2 and to delay biodegradation caused due to reaction of the base body 2 to the water 51. In other words, since the second protective layer 4, the first protective layer 3, and the base body 2 exhibit mechanisms different from each other, it is possible to lengthen the duration of biodegradability of the biocompatible alloy member 1.

Due to exhibition of the mechanisms described above, the biocompatible alloy member 1 used in the vascular stent 11 or the like is able to have lengthened duration of biodegradability in a case of being used in organisms. In other words, it is possible to realize service durability during a required period of time for various purposes including the vascular stent 11.

It is possible to use the biocompatible alloy member 1 in Embodiment 1 for various purposes, such as an artificial blood vessel, a suturing member for organisms, a vascular embolic coil, a binding member for organisms and a binding member for bones, in addition to the vascular stent 11. The biocompatible alloy member 1 need only be used by being processed to have a shape and a size corresponding to the purpose and the application location thereof.

Next, each part will be described in detail.

(Base Body)

The base body 2 is formed of a magnesium alloy. For example, the base body 2 is formed of a magnesium alloy realized by adding a mixture to magnesium. Therefore, the base body 2 has a composition in which various mixtures are suitably contained, while having magnesium as a major component.

The mixture contains at least one of predetermined rare earth elements.

Alternatively, the mixture contains at least one of predetermined non-rare earth elements. Alternatively, the mixture contains at least one of rare earth elements and at least one of non-rare earth elements.

Here, activation energy of the predetermined rare earth elements, which is energy when the rare earth elements are combined with oxygen and become an oxide, is 1,000 kJ/Mol or greater. In various rare earths, at least one of rare earths, of which the activation energy when becoming an oxide is 1,000 kJ/Mol or greater, is selected as a mixture.

The predetermined rare earth elements corresponding to the condition are any of Sc, Y, Dy, Sm, Ce, Gd, and La. In other words, a mixture contained in a magnesium alloy forming the base body 2 may be at least one of Sc, Y, Dy, Sm, Ce, Gd, and La.

In addition, activation energy of the predetermined non-rare earth elements, which is energy when the non-rare earth elements are combined with oxygen and become an oxide, is 1,000 kJ/Mol or greater. In various elements of non-rare earths, at least one of non-rare earths, of which the activation energy is 1,000 kJ/Mol or greater, is selected as a mixture.

The non-rare earth elements corresponding to the condition are any of Ti, Ta, Nb, Al, Mn, Fe, Cr, B, P, V, and Zr. In other words, a mixture contained in a magnesium alloy forming the base body 2 may be at least one of Ti, Ta, Nb, Al, Mn, Fe, Cr, B, P, V, and Zr.

As described above, a mixture contained in the magnesium alloy is at least one of Sc, Y, Dy, Sm, Ce, Gd, La, Ti, Ta, Nb, Al, Mn, Fe, Cr, B, P, V, and Zr.

Since the base body 2 contains a mixture thereof having the activation energy of 1,000 kJ/Mol or greater, an oxide or a hydroxide is reliably formed when reacting to water, so that it is possible to lengthen the duration of biodegradability related to reaction to water. Particularly, since a magnesium alloy forming the base body 2 contains a mixture of which the activation energy is 1,000 kJ/Mol or greater, it is possible to lengthen the duration of biodegradability.

Particularly, since activation energy is 1,000 kJ/Mol or greater, a strong oxidative effect is caused. Due to the oxidative effect, the base body 2 is likely to form an oxide enhancing service durability. As described above, the oxide becomes a protective layer, so that service durability of the biocompatible alloy member 1 is enhanced.

As above, the base body 2 is formed of a magnesium alloy having magnesium as a component. In this case, a magnesium alloy contains a mixture of at least one of Sc, Y, Dy, Sm, Ce, Gd, La, Ti, Ta, Nb, Al, Mn, Fe, Cr, B, P, V, and Zr. The elements are components selected from rare earths and non-rare earths. Due to the magnesium alloy containing the components as a mixture, the base body 2 is able to form an oxide generated due to reaction to water, even after the first protective layer 3 and the second protective layer 4 are exfoliated.

Since the oxide is formed on a surface of the base body 2, it is possible to delay corrosion caused due to reaction of the base body 2 to water. This is because an oxide continues to form a layer on a surface of the base body 2. The layer is able to exhibit a role as a protective layer of the base body 2.

In addition, in the base body 2, a mixture (including magnesium) is also able to form a hydroxide due to reaction to water inside an organism. In other words, the base body 2 is able to form at least one of an oxide and a hydroxide due to reaction to water. It is possible to lengthen the duration of biodegradability of the base body 2 by utilizing the formed oxide or hydroxide as a protective layer.

Particularly, since a mixture of which the activation energy is 1,000 kJ/Mol or greater is contained, an oxide due to reaction of the base body 2 to water is efficiently generated. Since an oxide is efficiently generated, it is possible to delay corrosion caused due to reaction of the base body 2 to water.

As a result of those described above, even after the first protective layer 3 and the second protective layer 4 are exfoliated, it is possible to lengthen the duration of biodegradability of the base body 2. The duration of biodegradability allows service durability for a required period of time to be realized, in a case where the biocompatible alloy member 1 is used in an artificial blood vessel, a vascular stent, a suturing member for organisms, a vascular embolic coil, a binding member for organisms, a binding member for bones, and the like.

(First Protective Layer)

The first protective layer 3 is formed on the outer side of the base body 2. Particularly, the first protective layer 3 need only be formed on a surface of the base body 2. The first protective layer 3 is formed of an oxide derived from the base body 2 or a complex of an oxide and a hydroxide derived from the base body 2. Due to such a composition, the first protective layer 3 becomes a stable layer and is able to reduce water reaching the base body 2.

In addition, the base body 2 is formed of a magnesium alloy containing a mixture of at least one of Sc, Y, Dy, Sm, Ce, Gd, La, Ti, Ta, Nb, Al, Mn, Fe, Cr, B, P, V, and Zr.

In addition, an oxide of the first protective layer 3 includes at least any of an oxide of magnesium, an oxide of rare earths, and an oxide of non-rare earths. Since the base body 2 is formed of a mixture including magnesium, predetermined rare earths, and predetermined non-rare earths, the first protective layer 3 includes at least any of an oxide of magnesium, an oxide of rare earths, and an oxide of non-rare earths contained in the base body 2. Due to the oxide, the first protective layer 3 becomes a stable layer.

As an example of the oxide described above, the first protective layer 3 contains any of $Sc_2O_3$, $Y_2O_3$, $Dy_2O_3$, $Sm_2O_3$, $CeO_2$, $Gd_2O_3$, and $La_2O_3$. Since these oxides are very elaborate, the first protective layer 3 becomes a very elaborate and stable layer.

In addition, a complex of an oxide and a hydroxide in the first protective layer 3 contains an oxide of magnesium and a hydroxide of magnesium. In addition, a complex thereof contains an oxide of rare earths and a hydroxide of rare earths. Due to such a composition, the first protective layer 3 becomes a stable layer.

For being a stable layer, the first protective layer 3 is able to reduce water reaching the base body 2.

(Second Protective Layer)

The second protective layer 4 is provided on the outermost circumference. In other words, the second protective layer 4 is provided on the outer side (surface) of the first protective layer 3. The second protective layer 4 is formed of a hydroxide derived from the base body 2. The hydroxide includes a hydroxide of magnesium. Alternatively, the hydroxide includes a hydroxide of rare earths.

The second protective layer 4 having such a composition becomes a very elaborate and stable layer. For being an elaborate and stable layer, the second protective layer 4 is able to reduce water reaching the base body 2.

As above, the second protective layer 4 is able to prevent corrosion caused due to water on the outermost circumference. Here, since the second protective layer 4 is a hydroxide, the second protective layer 4 is degraded under a bio-environment. In other words, the second protective layer 4 is degraded due to reaction to water such as body fluid in an organism. Due to the degradation, when the biocompatible alloy member 1 is applied to an organism, it is possible to prevent a harmful effect in which the biocompatible alloy member 1 is degraded under a bio-environment and remains in the organism longer than a predetermined period of time.

Cooperatively with the first protective layer 3, the second protective layer 4 is able to reduce and prevent infiltration of water into the base body 2 and to lengthen the service durability of the biocompatible alloy member 1. Particularly, due to a protective layer in which the first protective layer 3 and the second protective layer 4 having compositions and features different from each other are combined, it is possible to lengthen the duration of biodegradability of the biocompatible alloy member 1.

As described above, in the biocompatible alloy member 1 of Embodiment 1, it is possible to lengthen the duration of biodegradability due to protection in two stages sustaining protection by a combination of the first protective layer 3 and the second protective layer 4, and protection by a layer of an oxide or a hydroxide formed due to reaction of the base body 2 itself to water. As a result thereof, it is possible to use the biocompatible alloy member 1 for a required period of service in a case of being used for various purposes.

Embodiment 2

Next, Embodiment 2 will be described.
(Differences in Structure and Mechanism Compared to Technology in Related Art)
Differences in structure and mechanism compared to a biocompatible alloy member according to a technology in the related art will be described.

Figure 5:
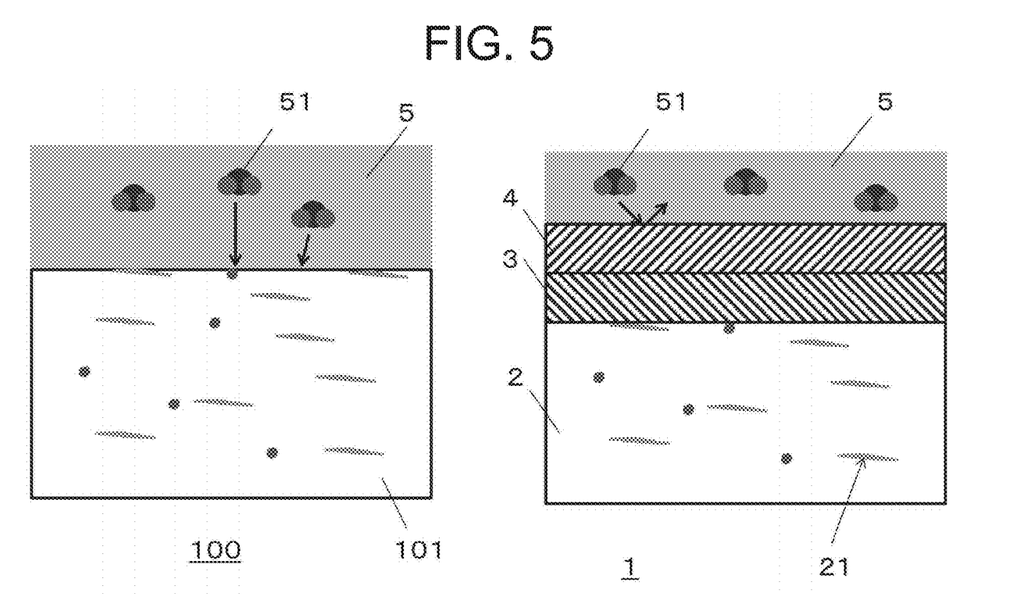
FIG. 5 is a view describing comparison between the biocompatible alloy member according to the present invention and a biocompatible alloy member according to a technology in the related art.

FIG. 5 is a view describing comparison between the biocompatible alloy member according to the present invention and a biocompatible alloy member according to a technology in the related art. On the left side in FIG. 5, a biocompatible alloy member 100 according to a technology in the related art is illustrated. On the right side of FIG. 5, the biocompatible alloy member 1 of the present invention is illustrated. The structure and the functions of the biocompatible alloy member 1 of the present invention are the same as described in Embodiment 1.

The biocompatible alloy member 100 according to a technology in the related art is configured to have only a base body 101. Therefore, as illustrated in FIG. 5, the base body 101 is directly exposed to the water 51. Since the water 51 is exposed, the base body 101 is likely to corrode.

The biocompatible alloy member 100 according to a technology in the related art is prioritized in ensuring strength of the base body 2. However, a concentrated phase of additives in the base body 101 or an intermetallic compound precipitated in crystal grain boundaries becomes a starting point of corrosion. The starting point causes development of corrosion, so that the base body 101 has short duration of biodegradability.

On the other hand, as illustrated on the right side in FIG. 5, the first protective layer 3 and the second protective layer 4 are provided on the outer side of the base body 2. In addition, the base body 2 is also formed of a magnesium alloy to which a mixture of predetermined rare earths or non-rare earths is added. Therefore, an element contained in the base body 2 reacts to the water 51 and is able to form at least one of an oxide and a hydroxide. Due to the layer formed of at least one of an oxide and a hydroxide, it is possible to delay corrosion of the base body 2 caused due to the water 51.

In this way, in comparison with a technology in the related art, due to the presence of the first protective layer 3 and the second protective layer 4, and characteristics in which a layer of an oxide or the like generated by a composition of the base body 2 is formed, it is possible to lengthen the duration of biodegradability of the biocompatible alloy member 1 of the present invention.

(Relationship between Service Durability and Usage Possibility)

Figure 6:
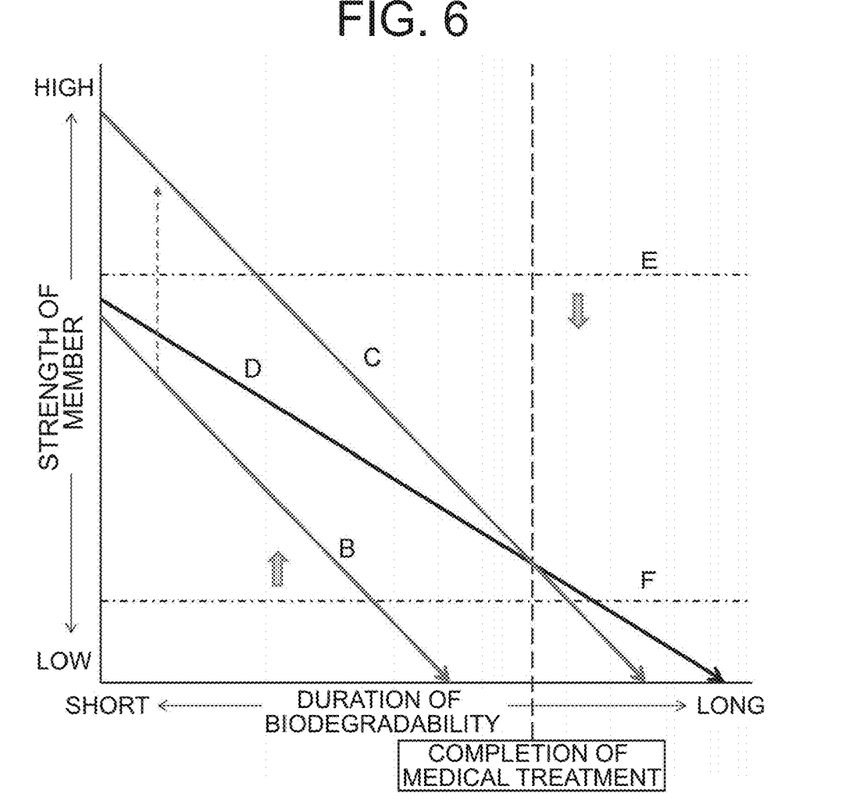
FIG. 6 is a graph illustrating a relationship between service durability and usage possibility of the biocompatible alloy member according to the present invention and the biocompatible alloy member according to a technology in the related art.

FIG. 6 is a graph illustrating a relationship between service durability and usage possibility of the biocompatible alloy member according to the present invention and the biocompatible alloy member according to a technology in the related art.

As described above as well as in Embodiment 1, the biocompatible alloy member 100 according to a technology in the related art has short duration of biodegradability and low service durability. Meanwhile, the biocompatible alloy member 1 of the present invention has long duration of biodegradability and high service durability. Due to the difference, the biocompatible alloy member 1 of the present invention is able to cope with a required therapeutic period when being used in an artificial blood vessel, a vascular stent, a suturing member for organisms, a vascular embolic coil, a suturing member for organisms, a suturing member for bones, and the like.

Artificial blood vessels and the like are required to corrode and dissipate when a predetermined therapeutic period is overdue, after being applied to an organism. If the therapeutic period comes to an end due to dissipation by corrosion, the organism becomes sustainable with original tissue of the organism. Meanwhile, if the biocompatible alloy member corrodes and dissipates before the therapeutic period comes to an end, it is difficult to take over and exhibit the function of original tissue of an organism.

In FIG. 6, the horizontal axis indicates the duration of biodegradability (indwelling period) of the biocompatible alloy member with respect to an organism. The vertical axis indicates strength of the biocompatible alloy member. The graph illustrates that the duration of biodegradability of the biocompatible alloy member becomes longer toward the right side of the horizontal axis. The graph also illustrates that strength of the biocompatible alloy member becomes higher toward the upper side of the vertical axis. FIG. 6 illustrates a correlationship between the strength of a member and the duration of biodegradability obtained by producing members according to a technology in the related art and the present invention in various degrees of strength and measuring the duration of biodegradability thereof.

In the biocompatible alloy member 100 (arrow B) according to a technology in the related art, in a case of strength with the size and the thickness which are able to be applied to a blood vessel or an organism, the duration of biodegradation is not able to reach the therapeutic period. In other words, the biocompatible alloy member 100 dissipates before the therapeutic period comes to an end. The arrow B in FIG. 6 illustrates the situation.

Meanwhile, in order to extend the duration of biodegradability of the biocompatible alloy member 100 according to a technology in the related art, the strength is required to be improved. The arrow C in FIG. 6 is a relational curve of the biocompatible alloy member 100 according to a technology in the related art having strength improved, with respect to the duration of biodegradability.

In a case of the biocompatible alloy member 100 according to a technology in the related art having strength increased as indicated with the arrow C, it is possible to ensure duration of biodegradability longer than the therapeutic period. However, in order to obtain the strength, the biocompatible alloy member 100 is required to be increased in thickness. For example, if the thickness is increased, it is difficult for the biocompatible alloy member 100 to be inserted or embedded into a blood vessel or biological tissue. For example, in a case of a vascular stent, the vascular stent is unlikely to be inserted into a predetermined lesion site due to a lack of flexibility. Therefore, the vascular stent is unlikely to be inserted into a blood vessel, or the inner diameter thereof becomes small even if the vascular stent is able to be inserted thereinto. Accordingly, it is difficult to ensure a blood flow, so that it is not possible to achieve the original object.

In FIG. 6, the dot-and-dash line E indicates a limit of applicability to organisms. In a case of realizing strength exceeding the limit, the member has a size or a thickness which is unlikely to be applied to an organism. In addition, in FIG. 6, the dot-and-dash line F indicates a lower limit value for the strength of a member required to the member. If the strength of a member falls below the lower limit value, it is not possible to exhibit a target function any longer.

In contrast, as indicated with the arrow D in FIG. 6, the biocompatible alloy member 1 of the present invention is able to realize strength which is applicable to an organism, and duration of biodegradability longer than the therapeutic period. It is possible to achieve both usage with respect to organisms and sustainment of an indwelling state in an organism while the therapeutic period is ensured.

In the case of the biocompatible alloy member 1 of the present invention, it is possible to sustain the therapeutic period, and the biocompatible alloy member 1 corrodes and dissipates after the elapse of the therapeutic period. Since a member such as a vascular stent used in organisms is required to dissipate after the therapeutic period ends, the biocompatible alloy member 1 also satisfies this condition. Moreover, there is no problem of difficulties in using the member with respect to an organism caused by increasing the strength as in the arrow C.

As above, in the biocompatible alloy member 1 of the present invention, dissimilar to the technologies in the related art, it is possible to realize service durability coping with a required therapeutic period, while having a thickness and a size usable in organisms.

Embodiment 3

Next, Embodiment 3 will be described.

Figure 7:
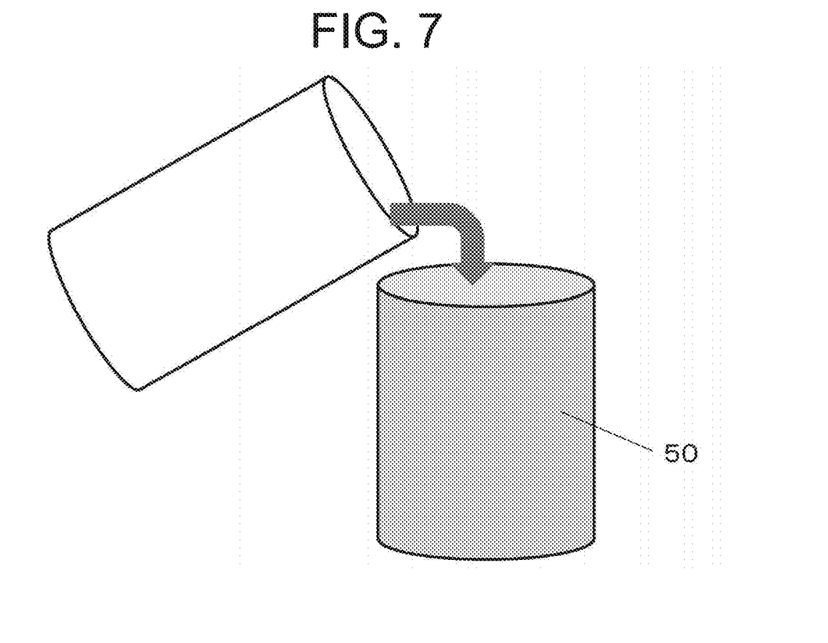
FIG. 7 is a schematic view illustrating a part of a production step for a biocompatible alloy member, that is, production of an alloy, in Embodiment 3 of the present invention.
Figure 8:
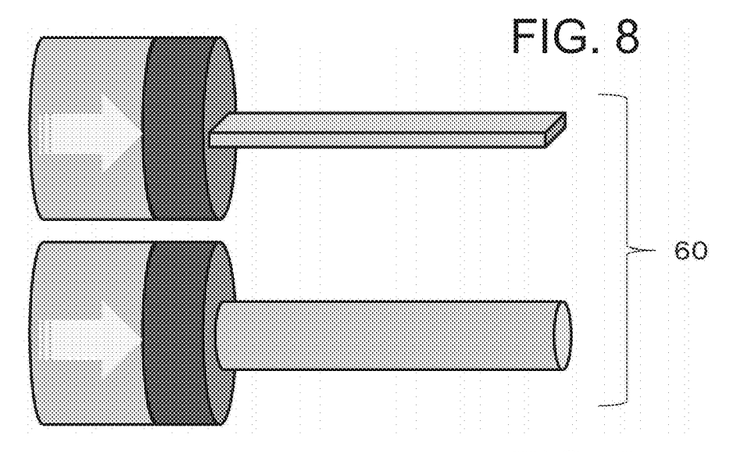
FIG. 8 is a schematic view illustrating a part of the production step for a biocompatible alloy member, that is, production of an alloy member, in Embodiment 3 of the present invention.
Figure 9:
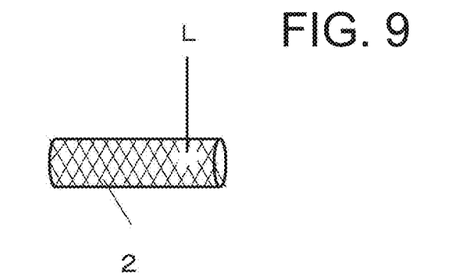
FIG. 9 is a schematic view illustrating a part of the production step for a biocompatible alloy member, that is, processing for a biocompatible member, in Embodiment 3 of the present invention.
Figure 10:
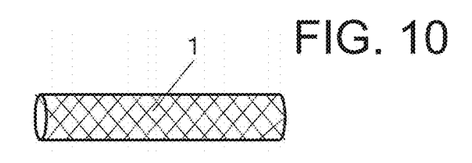
FIG. 10 is a schematic view describing a part of the production step for a biocompatible alloy member, that is, forming a protective membrane, in Embodiment 3 of the present invention.

In Embodiment 3, a production step of the biocompatible alloy member 1 in Embodiments 1 and 2 will be described. FIG. 7 is a schematic view illustrating a part of a production step for a biocompatible alloy member, that is, production of an alloy, in Embodiment 3 of the present invention. FIG. 8 is a schematic view illustrating a part of the production step for a biocompatible alloy member, that is, production of an alloy member, in Embodiment 3 of the present invention. FIG. 9 is a schematic view illustrating a part of the production step for a biocompatible alloy member, that is, processing for a biocompatible member, in Embodiment 3 of the present invention. FIG. 10 is a schematic view describing a part of the production step for a biocompatible alloy member, that is, forming a protective membrane, in Embodiment 3 of the present invention.

As illustrated in FIG. 7, first, an alloy for forming the base body 2 of the biocompatible alloy member 1 is produced. The alloy is a magnesium alloy, and magnesium and a predetermined mixture are put into a melting furnace 50. As illustrated in Embodiment 1, the mixture is a predetermined rare earth element or a predetermined non-rare earth element.

In the melting furnace 50, put raw materials are melted by being heated, are agitated, and the like, thereby producing an alloy for forming the base body 2. After being melted and the like, the raw materials are solidified and become an alloy.

Subsequently, as illustrated in FIG. 8, an alloy is processed into a plate/square bar 60 or the like through extrusion or forging. In other words, an alloy obtained in FIG. 7 is subjected to plastic processing and is thereby processed into an alloy member such as a plate. Strength of magnesium contained in a magnesium alloy is not high. In other words, strength of an alloy which only has passed through melting and solidification is deficient sometimes.

Therefore, strength of the magnesium alloy is improved by performing plastic processing such as extrusion, forging, or the like. If the plate/square bar 60 or the like is processed in the next step, it is possible to obtain a biocompatible member applicable to organisms.

FIG. 9 illustrates a state where the plate/square bar 60 or the like is processed and a biocompatible member 70 having a shape applicable to organisms is produced. The biocompatible member 70 is processed into a cylindrical shape or the like by rounding the plate/square bar 60 or forming an internal penetration hole. In addition, surface processing is also performed through laser processing L or the like. Through the processing, it is possible to obtain the base body 2 which becomes a biocompatible member having a shape applied as an artificial blood vessel, a vascular stent, or the like.

In FIG. 10, a first protective membrane 3 and a second protective membrane 3 are provided in the base body 2. It is possible to form the first protective membrane 3 and the second protective membrane 4 by generating an oxide or a hydroxide derived from the base body. Furthermore, after being subjected to surface treatment or sterilization treatment as necessary, it is possible to obtain the biocompatible alloy member 1. In this case, depending on the shape, the structure or the like, it is possible to obtain the biocompatible alloy members 1 corresponding to various purposes such as an artificial blood vessel and a vascular stent.

EXAMPLES

Examples will be described.

Example 1: Mg-2 Nd-1 Y-0.5 Mn-0.5 Zn-0.4 Zr

As Example 1, a biocompatible alloy member having Mg-2 Nd-1 Y-0.5 Mn-0.5 Zn-0.4 Zr was prepared. In the biocompatible alloy member of Example 1, a base body was formed with the composition of Mg-2 Nd-1 Y-0.5 Mn-0.5 Zn-0.4 Zr.

The base body was produced under the following production condition and surface treatment condition. The biocompatible alloy member of Example 1 was produced by forming a first protective layer and a second protective layer.

(Production Conditions)

An alloy ingot having the above-described composition was produced, and the ingot was caused to be a pillar member through extrusion. The pillar member was subjected to rolling, and a base body of a plate-shaped biocompatible alloy member was produced. In this case, the production conditions were as follows.

Ingot production condition: diameter of 70 mm, die casting Extrusion production condition: extrusion temperature of 400° C., extrusion ratio 25 Rolling condition: 350° C. Total pressure drop rate condition: 90% Annealing condition: 350° C.×30 min (Surface Treatment Condition)

The first protective layer and the second protective layer were formed on a surface of the base body produced under the production conditions described above by performing surface treatment. The conditions of the surface treatment were as follows.

The surface of the base body was subjected to mechanical polishing with abrasive paper (here, emery paper) of 1,000 mesh.

The base body was immersed in a nitric acid aqueous solution (5%) for 30 seconds.

After the base body was washed with pure water, acetone washing was performed for two minutes.

Figure 11:
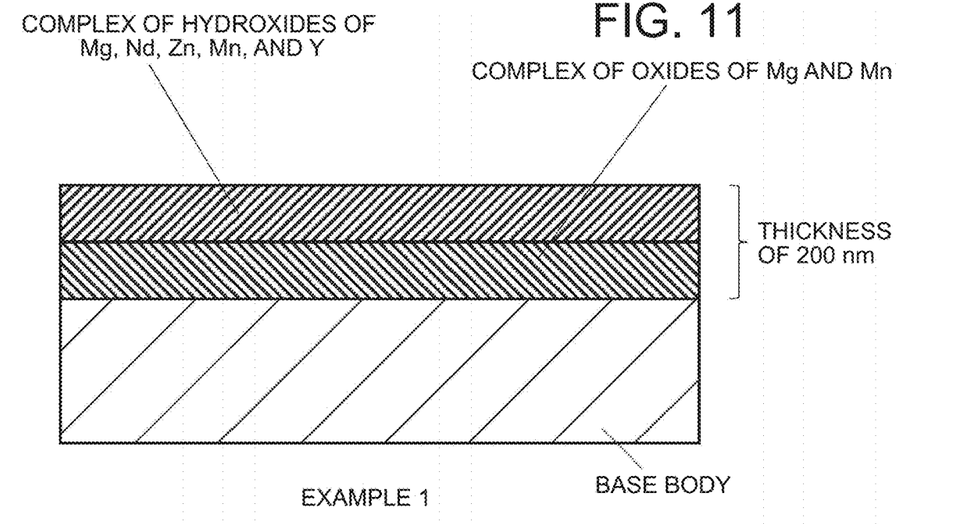
FIG. 11 is a schematic view of a biocompatible alloy member of Example 1 of the present invention.

The biocompatible alloy member of Example 1 produced under the above-described production condition and surface treatment condition is illustrated in FIG. 11. FIG. 11 is a schematic view of the biocompatible alloy member of Example 1 of the present invention. As illustrated in FIG. 11, the biocompatible alloy member of Example 1 includes a base body formed of a magnesium alloy having a composition of Mg-2 Nd-1 Y-0.5 Mn-0.5 Zn-0.4 Zr, a first protective layer formed of a complex of oxides of Mg and Mn on the base body, and a second protective layer formed of a complex of hydroxides of Mg, Nd, Zn, Mn, and Y on the first protective layer. The total membrane thicknesses of the first protective layer and the second protective layer were 200 nm.

Strength and service durability of the biocompatible alloy member of Example 1 were checked through a tension test and an immersion test.

(Tension Test)

Figure 12:
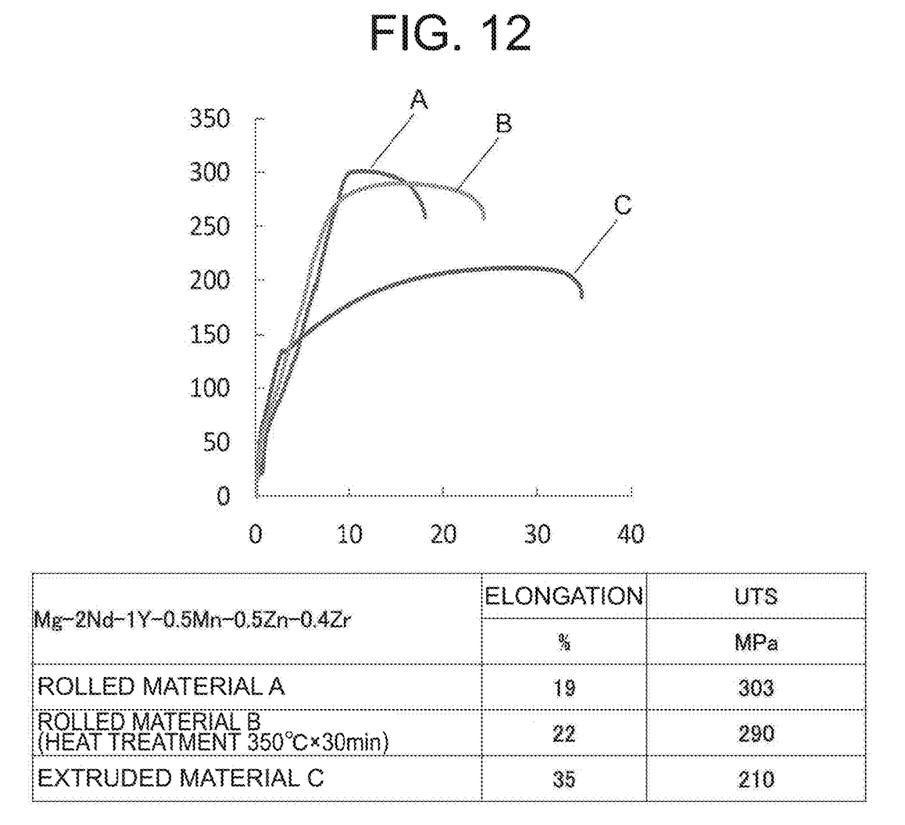
FIG. 12 is a graph and a table illustrating a result of a tension test of Example 1.

Test sample size of Example 1: plate having thickness of 1 mm, parallel portion 20 mm, distance between evaluation points 10 mm Tensile speed: 1 mm/min Test details: elongation percentage and UTS Test target (1) Example 1 produced up to the step of rolling (2) Example 1 produced up to the step of rolling and annealing (3) Extruded material FIG. 12 is a graph and a table illustrating a result of the tension test of Example 1. In the biocompatible alloy member of Example 1, tensile strength was measured for each of three materials, such as an "extruded material C" produced up to the step of extrusion under the production condition, a "rolled material A" produced up to the step of rolling under the production condition, and a "rolled material B (heat treatment)" produced up to the step of annealing under the production condition.

FIG. 12 illustrates the tensile strength of each of the three test samples. The elongation of the rolled material was 19%, the elongation of the rolled material (heat treatment) was 22%, and the elongation of the extruded material was 35%. In addition, the UTS of the rolled material was 303 MPa, the UTS of the rolled material (heat treatment) was 290 MPa, and the UTS of the extruded material was 210 MPa.

(Immersion Test)

The immersion test was performed under the following conditions.

Figure 13:
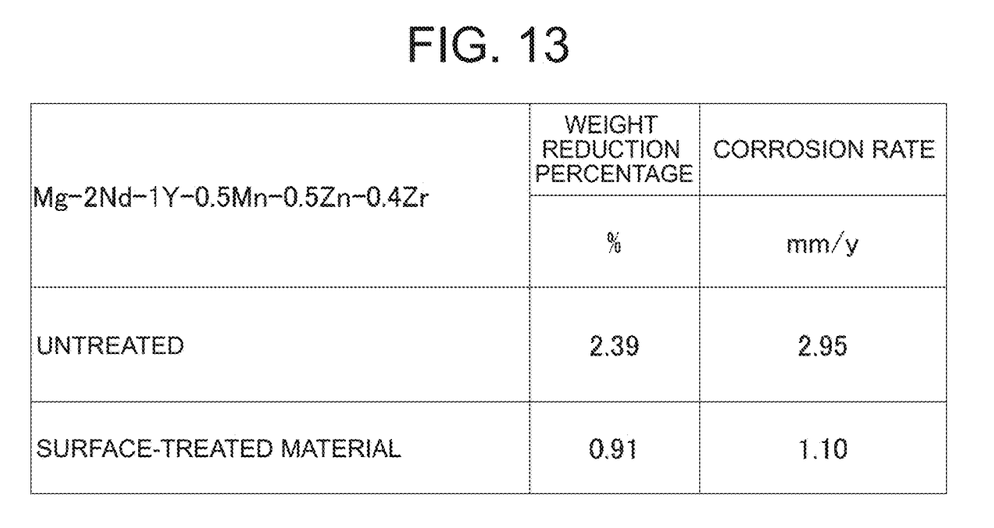
FIG. 13 is a table illustrating a result of an immersion test of Example 1.

Size of test sample of Example 1: 8×14×0.8 mm (plate-shaped) Immersion condition: immersed in fetal bovine serum at 37° C. for one day FIG. 13 illustrates the result of the immersion test under the conditions. FIG. 13 is a table illustrating the result of the immersion test of Example 1. Here, the immersion test was individually performed for the test sample (untreated) of Example 1 which was not subjected to the above-described surface treatment, and the test sample (surface-treated material) of Example 1 which was subjected to surface treatment.

The weight reduction percentage of the untreated test sample was 2.39%, and the corrosion rate was 2.95 mm/y. The weight reduction percentage of the test sample (surface-treated material) was 0.91%, and the corrosion rate was 1.10 mm/y.

As seen from the result of the immersion test, corrosion was delayed and service durability was improved by performing surface treatment and providing the first protective layer and the second protective layer.

As above, from each of the tension test and the immersion test, it was checked that Example 1 complying with the scope of the present invention had high strength and service durability.

Example 2: Mg-2.5 Nd-1 Gd-0.4 Zr

As Example 2, a biocompatible alloy member having Mg-2.5 Nd-1 Gd-0.4 Zr was prepared. In the biocompatible alloy member of Example 2, a base body was formed with the composition of Mg-2.5 Nd-1 Gd-0.4 Zr.

The base body was produced under the following production condition and surface treatment condition. The biocompatible alloy member of Example 2 was produced by forming a first protective layer and a second protective layer.

(Production Conditions)

An alloy ingot having the above-described composition was produced, and the ingot was caused to be a pillar member through extrusion. The pillar member was subjected to rolling, and a base body of a plate-shaped biocompatible alloy member was produced. In this case, the production conditions were as follows.

Ingot production condition: diameter of 70 mm, die casting Extrusion production condition: extrusion temperature of 400° C., extrusion ratio 25 Rolling condition: 350° C. Total pressure drop rate condition: 90%

(Surface Treatment Condition)

The first protective layer and the second protective layer were formed on a surface of the base body produced under the production conditions described above by performing surface treatment. The conditions of the surface treatment were as follows.

The surface of the base body was subjected to mechanical polishing with abrasive paper (here, emery paper) of 1,000 mesh.

The base body was immersed in a nitric acid aqueous solution (5%) for 30 seconds. After the base body was washed with pure water, acetone washing was performed for two minutes.

Figure 14:
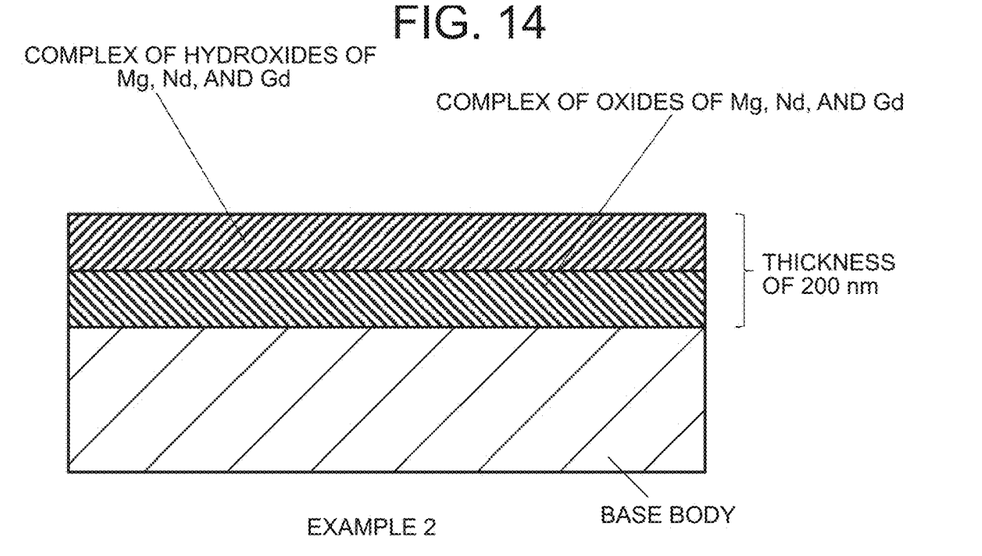
FIG. 14 is a schematic view of a biocompatible alloy member of Example 2 of the present invention.

The biocompatible alloy member of Example 2 produced under the above-described production condition and surface treatment condition is illustrated in FIG. 14. FIG. 14 is a schematic view of the biocompatible alloy member of Example 2 of the present invention. As illustrated in FIG. 14, the biocompatible alloy member of Example 1 includes a base body formed of a magnesium alloy having a composition of Mg-2.5 Nd-1 Gd-0.4 Zr, a first protective layer formed of a complex of oxides of Mg, Mn, and Gd on the base body, and a second protective layer formed of a complex of hydroxides of Mg, Nd, and Gd on the first protective layer. The total membrane thicknesses of the first protective layer and the second protective layer were 200 nm.

Service durability of the biocompatible alloy member of Example 2 was checked through an immersion test.

(Immersion Test) The immersion test was performed under the following conditions.

Figure 15:
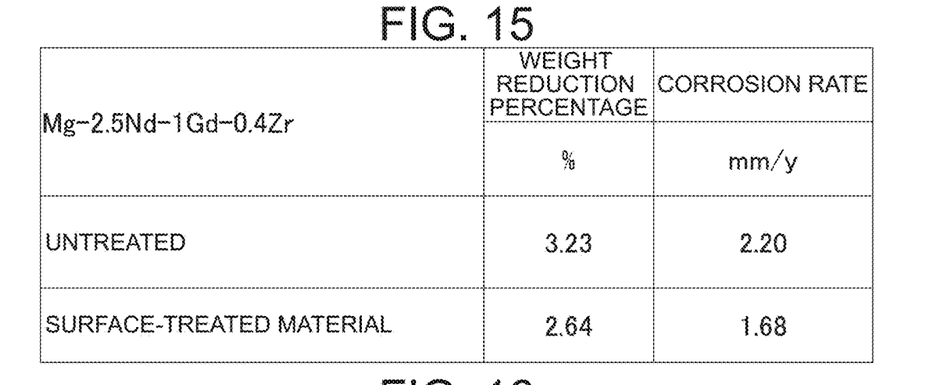
FIG. 15 is a table of a result of an immersion test of Example 2.

Size of test sample of Example 2: 8×14×0.8 mm (plate-shaped) Immersion condition: immersed in fetal bovine serum at 37° C. for one day FIG. 15 illustrates the result of the immersion test under the conditions. FIG. 15 is a table of the result of the immersion test of Example 2. Here, the immersion test was individually performed for the test sample (untreated) of Example 2 which was not subjected to the above-described surface treatment, and the test sample (surface-treated material) of Example 2 which was subjected to surface treatment.

The weight reduction percentage of the untreated test sample was 3.23%, and the corrosion rate was 2.20 mm/y. The weight reduction percentage of the test sample (surface-treated material) was 2.64%, and the corrosion rate was 1.68 mm/y.

As seen from the result of the immersion test, corrosion was delayed and service durability was improved by performing surface treatment and providing the first protective layer and the second protective layer.

As above, from the immersion test, it was checked that Example 2 complying with the scope of the present invention had high service durability.

Example 3: Mg-2 Nd-1 Y-0.5 Mn-0.5 Zn-0.4 Zr

As Example 3, a biocompatible alloy member having Mg-2 Nd-1 Y-0.5 Mn-0.5 Zn-0.4 Zr was prepared. In the biocompatible alloy member of Example 2, a base body was formed with the composition of Mg-2 Nd-1 Y-0.5 Mn-0.5 Zn-0.4 Zr.

The base body was produced under the following production condition and surface treatment condition. The biocompatible alloy member of Example 3 was produced by forming a first protective layer and a second protective layer.

(Production Conditions)

An alloy ingot having the above-described composition was produced, and the ingot was caused to be a rod-shaped member through extrusion. After the rod-shaped member was subjected to extrusion again, drawing and heat treatment were repetitively performed, and a linear base body of the biocompatible alloy member was produced. In this case, the production conditions were as follows.

Ingot production condition: diameter of 70 mm, die casting Extrusion production condition (first stage): extrusion temperature of 400° C., extrusion ratio 25 Extrusion production condition (second stage): extrusion temperature of 450° C., extrusion ratio 25 Drawing condition: total area reduction rate of 75%, annealing temperature of 400° C.

(Surface Treatment Condition)

The first protective layer and the second protective layer were formed on a surface of the base body produced under the production conditions described above by performing surface treatment. The conditions of the surface treatment were as follows.

The base body was immersed in a nitric acid aqueous solution (0.5%) for 30 seconds while applying ultrasound waves. After the base body was washed with pure water, acetone washing was performed for one minute.

The biocompatible alloy member of Example 3 produced under the above-described production condition and surface treatment condition has a surface structure similar to that in the schematic view of the biocompatible alloy member of Example 1 according to the present invention.

Service durability of the biocompatible alloy member of Example 3 was checked through an immersion test.

(Immersion Test)

The immersion test was performed under the following conditions.

Size of test sample of Example 3: 1 (diameter)×20 mm (linear)

Figure 16:
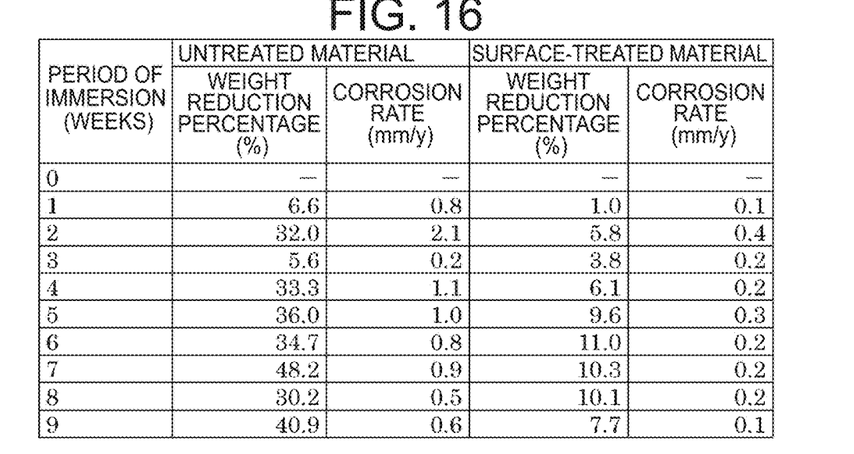
FIG. 16 is a table of a result of an immersion test of Example 3.

Immersion condition: immersed in a culture medium (DMEM+fetal bovine serum of 10%) at 37° C., under $CO_2$ (5%) for two months FIG. 16 illustrates the result of the immersion test under the conditions. Here, after drawing, the immersion test was individually performed for the test sample (untreated material) of Example 3 which was not subjected to the above-described surface treatment, and the test sample (surface-treated material) of Example 3 which was subjected to surface treatment.

The weight reduction percentage of the untreated test sample was 40.9% in the ninth week, and the corrosion rate was 0.6 mm/y. The weight reduction percentage of the test sample (surface-treated material) was 7.7% in the ninth week, and the corrosion rate was 0.1 mm/y.

As seen from the result of the immersion test, corrosion was delayed for a long period of time and service durability was improved by performing surface treatment and providing the first protective layer and the second protective layer.

As above, from the immersion test, it was checked that Example 3 complying with the scope of the present invention had high service durability.

As above, as seen from the result of the experiments of Examples 1 to 3, a biocompatible alloy member, which is produced with the composition according to the scope of the present invention and has the first protective layer and the second protective layer, has high strength and service durability.

From the result of the experiments of Examples 1 to 3, it is adequate for a base body to have a composition as follows.

The base body has a composition containing Nd ranging from 0.5 to 5.0 percent by weight, Y ranging from 0.1 to 5.0 percent by weight, Mn ranging from 0.1% to 1.0%, Zn ranging from 0.1 to 4.0 percent by weight, and Zr ranging from 0.1 to 1.0 percent by weight.

Alternatively, the base body contains Nd ranging from 0.5 to 5.0 percent by weight, Gd ranging from 0.1 to 5.0 percent by weight, and Zr ranging from 0.1 to 1.0 percent by weight.

The biocompatible alloy members described in Embodiments 1 to 3 are examples for describing the gist of the present invention. The present invention includes changes and modifications within a range not departing from the scope of the gist thereof.

REFERENCE SIGNS LIST

1 BIOCOMPATIBLE ALLOY MEMBER
2 BASE BODY
3 FIRST PROTECTIVE LAYER
4 SECOND PROTECTIVE LAYER
11 VASCULAR STENT

What is claimed is:

1. An alloy member usable in organisms, comprising:
a base body that contains a magnesium alloy of magnesium and a mixture containing Nd, Y, Mn, Zn and Zr;
a first protective layer that contains a complex of oxides of magnesium and Mn; and a second protective layer that contains a complex of hydroxides of magnesium, Nd, Zn, Mn and Y.

2. The alloy member usable in organisms according to claim 1,
wherein the first protective layer is on a surface of the base body, and
wherein the second protective layer is on a surface of the first protective layer.

3. The alloy member usable in organisms according to claim 1,
wherein the base body contains Nd ranging from 0.5 to 5.0 percent by weight, Y ranging from 0.1 to 5.0 percent by weight, Mn ranging from 0.1 to 1.0 percent by weight, Zn ranging from 0.1 to 4.0 percent by weight, and Zr ranging from 0.1 to 1.0 percent by weight.

4. The alloy member usable in organisms according to claim 1,
wherein the alloy member is used in at least one of an artificial blood vessel, a stent, a suturing material for organisms, a vascular embolic coil, a clip, an encapsulant, a binding material for organisms, a binding material for bones, a mesh sheet, a correction material for bones, a solid or porous support material for bones, and a scaffold in which cells are retained and proliferate inside an organism.

5. A bio-implantation device, comprising
a structural member comprised of the alloy member usable in organisms according to claim 1,
wherein the bio-implantation device is biodegradable.

6. A production method for an alloy member usable in organisms, comprising:

a step of preparing a base body that contains a magnesium alloy of magnesium and a mixture containing Nd, Y, Mn, Zn and Zr;
a step of forming a first protective layer, which contains a complex of oxides of magnesium and Mn; and
a step of forming a second protective layer, which contains a complex of hydroxides of magnesium, Nd, Zn, Mn and Y, on the first protective layer.

7. An alloy member usable in organisms, comprising:
a base body that contains a magnesium alloy of magnesium and a mixture containing Nd, Gd and Zr;
a first protective layer that contains a complex of oxides of magnesium, Mn and Gd; and
a second protective layer that contains a complex of hydroxides of magnesium, Nd and Gd.

8. The alloy member usable in organisms according to claim 7,
wherein the base body contains Nd ranging from 0.5 to 5.0 percent by weight, Gd ranging from 0.1 to 5.0 percent by weight, and Zr ranging from 0.1 to 1.0 percent by weight.

9. A production method for an alloy member usable in organisms, comprising:
a step of preparing a base body that contains a magnesium alloy of magnesium and a mixture containing Nd, Gd and Zr;
a step of forming a first protective layer, which contains a complex of oxides of magnesium, Mn and Gd; and
a step of forming a second protective layer, which contains a complex of hydroxides of magnesium, Nd and Gd, on the first protective layer.

* * * * *